United States Patent [19]

Silverstein et al.

[11] 4,034,080

[45] July 5, 1977

[54] CHEMICAL ATTRACTANT FOR SMALLER EUROPEAN BARK BEETLE

[75] Inventors: Robert M. Silverstein; William E. Gore; Glenn T. Pearce, all of Syracuse, N.Y.; Roy A. Cuthbert, Delaware, Ohio; John B. Simeone; Gerald N. Lanier, both of Syracuse, N.Y.; John W. Peacock, Marion, Ohio

[73] Assignee: The United States of America as represented by the Secretary of Agriculture, Washington, D.C.

[22] Filed: Jan. 14, 1976

[21] Appl. No.: 648,835

[52] U.S. Cl. .................................. 424/84; 424/213; 424/283; 424/306; 424/352; 424/354
[51] Int. Cl.² ........................................ A01N 17/14
[58] Field of Search ...................................... 424/84

[56] References Cited

UNITED STATES PATENTS 3,755,563  8/1973  Vite ..................................... 424/84

OTHER PUBLICATIONS

Martin; *Journal of Economic Entomology*, 29(2): 297-306, (Nov. 1935).
Meyer et al.; *Annals Entomological Society of America*, 60(3):642-647 (May 1967).
Peacock et al., *Annals Entomological Society of America*, 64(5): 1143-1149 (Sept. 1971).
Byrne et al; *J. Chem. Ecology*, 1(1):1-7, (1975).
Peacock et al.; *J. Chem. Ecology*, 1(1) 149-160, (1975).
Moeck; *Canadian Entomologist* 102:792-796 (1970).
Dull et al; *J. Organic Chem.*, 34(9):2543-2549, (Sept. 1969).
Ohta et al.; *Tetrahedron Letters*, 51:6365-6370, (1966).
Piers et al.; *Canadian Journal of Chem.*, 49:12-19, (1971).
Tanaka et al.; *J. Chem. Society Perkin I*; 1721-1727, (1972).
Ohta et al.; *Tetrahedron Letters*, 51:6365-6370, (1966).
Vlahov et al.; *Collection Czechoslovak Chem. Communications*, 32:808-821, (1967).

*Primary Examiner*—Allen J. Robinson
*Attorney, Agent, or Firm*—M. Howard Silverstein; David G. McConnell

[57] ABSTRACT

A method is described for combating the bark beetle Scolytus multistriatis. The method uses an attractant mixture of three compounds: 4-methyl-3-heptanol; 2,4-dimethyl-5-ethyl-6,8-dioxabicyclo (3.2.1) octane; and α-cubebene. Traps containing the mixture are set out in or near infested areas. When a sufficient number of beetles have been lured into the traps, they are removed and destroyed. Alternatively, the traps contain an insecticide which enables the traps to remain onsite for a longer period.

4 Claims, No Drawings

CHEMICAL ATTRACTANT FOR SMALLER EUROPEAN BARK BEETLE

BACKGROUND OF THE INVENTION

1. Field of the Invention

This invention relates to the control of Dutch Elm disease. More particularly the invention concerns a method for regulating the aggregation of the bark beetle *Scolytus multistriatus* which exploits a mixture of three compounds used alone or in combination with compatible biocides in order to simultaneously attract and combat the beetle.

2. Description of the Prior Art

Dutch Elm disease has devastated elm populations in the northeastern United States and presently threatens American elms throughout their natural and cultivated range. The smaller European elm bark beetle *Scolytus multistriatus* (Marsham) is the principal vector for the Dutch Elm disease pathogen, *Ceratocystis ulmi*.

The need for a strong force which could be harnessed to aggregate this beetle has been apparent for some time. This beetle now ranks among the most pernicious tree destroyers. Wholesale spraying of the habitats of these insects with even the most baneful of pesticides usually proves to be a futile, if not deleterious exercise, since bark beetles spend most of their time safely situated underneath tree bark where they mate and reproduce and rear their young. Indeed, indiscriminate spreading of toxic chemicals may do more harm than good if many other animals predacious of beetles come into contact with the lethal spray deposits while seeking their prey. The predators may thus be deterred if not totally eliminated before they can execute this natural function of capturing and destroying the young beetles of a new brood as they emerge from a tree. Chemical control of this sort has been further complicated by difficulty in locating the beetle infestations before a new brood has dispersed to other areas.

Investigations by Martin (1936)[1], Meyer and Norris (1967)[2], and Peacock, et al. (1971)[3] have shown that adult elm bark beetles are weakly attracted to uninfested elm wood.

Several years ago it was determined that Scolytus produces an aggregation pheromone. Research has thus focused on developing a synthetic simulation of this pheromone which could be used for bait in mortality traps. A pheromone is an animal attractant secretion that affects another of its own species. Typically beetle pheromones serve as chemical messengers directing other beetles to a receptive mate, palatable fare and/or a comfortable place in which to lay eggs. The report by Peacock, et al. (1971) demonstrated that secondary mass attack by both sexes of beetles on potential breeding sites is directed by an aggregation pheromone produced by virgin females boring into the phloemcambial region of weakened elm trees. The chemical composition of this pheromone has until the present time been unknown.

SUMMARY OF THE INVENTION

The present invention resides in the discovery of various mixtures of three compounds: 4-methyl-3-heptanol (referred to herein as I); 2,4-dimethyl-5-ethyl-6,8-dioxabicyclo (3.2.1) octane (referred to as II); and α-cubebene (III). While a mixture comprised of all three of the compounds is far superior to any other, mixtures comprised of I and II, and I and III have shown to be effective and, to a lesser extent a mixture comprised of II and III.

The invention also lies in the utilization of these mixtures in combination with an agent for animal control, e.g., with animal traps or insecticides. These mixtures may be prepared by synthetic methods including the II component, whose novel structure has been confirmed by synthesis. Alternatively, synthetic I and II plus natural III (from cubeb oil) has been proven highly effective. The primary object of this invention is the provision of a method of attracting the bark beetle Scolytus in order to detect and control infestations thereof. More particularly the object of this work is to develop a simulative aggregation pheromone which can be used efficiently, safely and inexpensively to control Dutch Elm disease-carrying beetles. Further objects of the invention will be evident from the following description.

DESCRIPTION OF THE PREFERRED EMBODIMENT

The total attractant source was a pentane extract of Porapak Q, a solid absorbant used to collect organic volatiles from aerated chambers containing virgin female-infested elm bolts. Byrne, et al. (1975)[4] demonstrates the general applicability of Porapak Q as a trapping agent for collection of insect pheromones by aeration.

Each infestation of 4,000–7,000 virgin females was aerated continuously for 7 days beginning at the third day after introduction in order to coincide with the period of maximum pheromone production. The Porapak extracts were concentrated under a fractional distillation column (glass bead packing) and the concentrates were fractionated by preparative GLC. The fractionation schemes were monitored in the laboratory by the arrestant-existant bioassay (Peacock et al. 1975)[5] and by an attractant bioassay with an alfactometer described by Moeck and Peacock (1970)[6].

Biological activity of the original Parapak extract could be approximated only by recombination of three of the seven initial GLC fractions (SE-30), each of which yielded one of the three active components after successive GLC fractionation on Carbowax 20M, a polar polymer, and Apiezon L, a nonpolar hydrocarbon, columns. The activities of all possible combinations of compounds I, II, and III relative to the Porapak extract were determined by the bioassays mentioned above (Table I). The laboratory bioassays clearly indicate that none of the compounds is active individually, that various combinations of the three are effective in varying degrees, and that a mixture of all three of the compounds yields activity nearly equivalent to that of the Porapak extract.

Table I

| | | Laboratory Bioassays of Attractant Components | | | | |
|---|---|---|---|---|---|---|
| | | Dosage per replicate (nanograms) Compounds | | | Mean percent response | |
| Test | Materials Tested | I | II | III | Bioassay (1) | Bioassay (2) |
| a | I | 25 | — | — | 0 | 7.0 |
| b | II | — | 19 | — | 1.3 | 3.0 |
| c | III | — | — | 50 | 2.7 | 9.0 |
| d | I + II | 25 | 19 | — | 22.7 | 18 |
| e | I + III | 25 | — | 50 | 17.3 | 15 |
| f | II + III | — | 19 | 50 | 2.7 | 13 |
| g | I + II + III | 25 | 19 | 50 | 46.0 | 44 |
| h | Porapak extract | 25 | 19 | 50 | 45.3 | 54 |

Table I-continued
Laboratory Bioassays of Attractant Components

| Test | Materials Tested | Dosage per replicate (nanograms) Compounds I | II | III | Mean percent response Bioassay (1) | Bioassay (2) |
|---|---|---|---|---|---|---|
| i | n-Hexane | — | — | — | 0 | 0 |

Virgin female S. multistriatus beetles retrieved from elm bolts within 3 to 5 days after infestation were mixed with powdered dry ice and mascerated with a mortar and pestle. A pentane extract of the mascerated beetle tissue was analyzed by GLC for compounds I, II, and III. Positive identifications for compounds I and II were obtained on two analytical columns (6.1 m Carbowax 20M, 6.1 m Apiezon L), but only a trace of III was observed. Similar analyses of a hexane-Waring blender extract of uninfested elm tissue (xylem and phloem strips) and a Porapak extract from the aeration of uninfested elm bolts yielded compound III, but no detectable quantities of I or II. On the basis of these results, we conclude that I and II are beetle-produced pheromones, and that III is a host-produced synergist.

Quantitative GLC analyses of several Porapak extracts from aeration of virgin females on logs indicated that the release ratio of I to II was consistently 1:1. The ratio of I or II to III, however, was variable between 1:2 and 1:10.

Compound I was identified as 4-methyl-3-heptanol ($[\alpha]D^{26}$ −15°) by comparison of its MS, IR, and NMR spectra with those of a synthetic sample prepared by sodium borohydride reduction of 4-methyl-3-heptanone (Aldrich Chemical Co.). Since 4-methyl-3-heptanol contains two chiral centers, the synthetic material exists as two diastereomeric forms; however only one form is produced by the female beetle. The synthetic diastereomers are separable by gas chromatography, with the natural alcohol corresponding to the diastereomer of shorter retention time on a Carbowax 20M column. Compound I was shown to be a single enantimer by comparison of the $^1H$ and $^{19}F$ NMR spectra of the Mosher derivatives (esters of R (+) α-methoxy-α-trifluoromethyl phenylacetric acid) (Dale 1969)[7] of racemic I with those of natural I.

The novel structure assigned to compound II is consistent with the MS, IR, and NMR spectra. The carbon skeleton of II was determined by hydrogenolysis on palladium. The mass spectra of the hydrogenolysis products separated by gas chromatography were identical with those of authentic samples of 3,5-dimethylocatane, 2,4-dimethylheptane, and with the published mass spectrum of 4-methylheptane.

The spectra of a fourth compound isolated from the Porapak extract and inactive in the laboratory bioassay were also consistent with the ketal structure assigned to II. Structure II can theoretically exist as four diastereomers by inversion of stereochemistry at carbons 2 and 4 relative to carbon 1, thereby suggesting that the fourth compound is a diastereome of II. The active and inactive ketals have been assigned the trivial names of α- and β-multistriatin, respectively.

The gross structure of α- and β-multistriatin was confirmed by synthesis. The MS, IR, NMR spectra of natural α- and β-multistriatin were congruent with those of the synthesized compounds.

Compound III ($[\alpha]D$ −24°) was identified as α-cubebene, a known sesquiterpene whose structure and absolute stereochemistry have been rigorously determined (Ohta, et al. 1966[8], Piers, et al. 1971[9], Tanaka, et al. 1972[10]). The MS, IR, and NMR spectra of isolated III matched those of an authentic sample of α-cubebene and the specific rotation was in accord with the literature value ($[\alpha]D$ −20.0°); Ohta (1966[11], Vlakhov (1967)[12]. In addition, GLC comparison by coinjection on 100' Carbowax and 50' Apiezon L columns further supported the assignment of III as α-cubebene. Quantities of α-cubebene sufficient for field tests were obtained by distillation of cubeb oil[11] through a 40-plate spinning band fractional distillation column, with the purest fraction (1 ml, b.p. 30° −32° C, 1.3 mm Hg) containing 90% α-cubebene.

The field tests were conducted in a residential section of Charlotte, North Carolina. The test was designed to indicate the relative attractiveness of three pheromone preparations. These were:
1. Porapak Aeration Extract (PE).
2. Attractant Mixture (AM).
   a. synthetic 4-methyl-3-heptanol (<99%), a 50/50 mixture of diastereomers.
   b. GLC purified synthetic α-multistriatin (99%).
   c. α-cubebene (90%), distilled from cubeb oil.
3. Multilure - Crude Attractant Mixture (CAM).
   a. 4-methyl-3-heptanol (<99%), Aldrich Chemical Co., a 55/45 mixture of diastereomers.
   b. crude synthetic multistriantin (90%), a 40/60 mixture of α-and β-multistriatin.
   c. cubeb oil, containing 10% α-cubebene.

A paired comparison test was used to evaluate the relative attractiveness of the three attractant preparations. A total of 30 trapping sites were employed with 10 sites for each of the following paired comparisons: PE vs AM, PE vs Multilure, AM vs Multilure. Each trap site consisted of two traps hung at one tree on opposite sides of the main bole. The traps were 31 cm square hardware cloth (6 mm X 6 mm mesh) coated with Stikem Special, a sticky rubbery material, baited at the center with 2.5-ml polyethylene snap-cap vials containing one of the three attractant preparations. The vials were loaded and sealed with the attached cap 3 days prior to placement in the field. Positional effects were minimized by exchanging the positions of the traps at each site after the first day of trapping. Trap catches for the 48-hour test period are summarized in Table II.

TABLE II
Comparative field evaluation of attractant mixtures for Scolytus multistriatus
Trap Catches: Each entry is a total for the 10 traps used for each material indicated.

| Date | PE vs AM | | PE vs Multilure | | AM vs Multilure | |
|---|---|---|---|---|---|---|
| | | | Paired comparisons | | | |
| 4/30 | 690 | 766 | 1164 | 843 | 929 | 1268 |
| 5/1 | 356 | 724 | 465 | 897 | 865 | 645 |
| Total | 1046 | 1490 | 1629 | 1740 | 1794 | 1913 |

| Total beetles caught on: | |
|---|---|
| PE (20 traps): | 2675 |
| AM (20 traps): | 3284 |
| Multilure (20 traps): | 3653 |

The methods of destroying invertebrate animals, particularly bark beetles, using the attractants of the invention fall into two categories: concentration methods and dispersal methods through confusion. Methods vary in accordance with the forest practices applied. By one concentration method, insects are attracted to host trees by use of the attractants of the invention which are then harvested carrying away the beetle population to the sawmill where they are destroyed in the debarker. By another concentration method, the insects are attracted to resistant or unsuitable hosts that do not permit brood development. Another effective concentration method is the attraction of the insects to suitable hosts using the attractants of the invention which are treated with chemicals either destructive to the insects or detrimental to broad development. Biocides for use in this invention may be any of the common materials known to kill bark beetles. Illustrative of the wide variety of insecticides which may be used with the attractants of this invention are the following: DDT, lindane, allethrin, chlordane, malathion, and rotenone. Insecticides, of course, can be effectively used in traps or on trees baited with the attractants of the invention. This eliminates the need to spread the insecticides unnecessarily and helps prevent killing useful insects and other animals.

Practical use of the attractants of the invention is also made in insect surveys where traps are baited with the attractants. The catches indicate the size and location of infestation; economical use of appropriate pest management systems can then be determined.

The idea behind the dispersal methods or pheromone masking is, instead of orienting the insects to a trap, to control their sex life by keeping them from finding each other. For example, one technique of pheromone masking would be to permeate the atmosphere with the pheromone. This prevents the males of the species from orienting to and inseminating females. Field trials have indicated that economic control of some insects over large areas may be possible with this method using the attractants of the invention.

The attractants of this invention may be used per se for other purposes without the addition of a poison. They may serve, for example, to guide certain insects in the fertilization of plants, one of the desirable functions some of them may perform. They may also be made use of in controlling the flight, in the issuing of warnings for the protection of trees and other plants, and in research on population dynamics.

The attractants of the invention may be used in actual practice in the field in different ways as is known in the art. They may be formulated with other materials or impregnated on a carrier or used in traps or similar devices different from the ones described above. As various changes could be made in the above compositions and methods without departing from the scope of the invention, it is intended that all matter contained in the above description shall be interpreted as illustrative and not in a limiting sense.

NOTES

[1] Martin, Charles H. *Preliminary Report of Trap-Log Studies on Elm Bark Beetles*. In Journal of Economic Entomology. 29(2):297–306. November 1955.

[2] Meyer, H. J., and D. M. Norris. *Behavioral Responses by Scholytus multistriatus (Coleoptera: Scolytidae) to Host-(Ulmus) and Beetle-Associated Chemotactic Stimuli*. In Annals of the Entomological Society of America. 60(3):642–647. May 1967.

[3] Peacock, John W., A. Charles Lincoln, John B. Simeone, and Robert M. Silverstein. *Attraction of Scolytus multistriatus (Cleoptera: Scolytidae) to a Virgin-Female-Produced Pheromone in the Field*. In Annals of the Entomological Society of America. 64(5):1143–1149. September 1971.

[4] Byrne, Kevin J., Willian E. Gore, Glenn T. Pearce, and Robert M. Silverstein. *Porapak-Q Collection of Airborne Organic Compounds Serving as Models for Insect Pheromones*. In Journal of Chemical Ecology. 1(1):1–7. 1975.

[5] Peacock, J. W., R. A. Cuthbert, W. E. Gore, G. N. Lanier, G. T. Pearce, and R. M. Silverstein. *Collection on Porapak Q of the Aggregation Pheromone of Scolytus multistriatus (Coleoptera: Scolytidae)*. In Journal of Chemical Ecology. 1(1):149–160. 1975.

[6] Moeck, Henry A. *An Olfactometer for the Bio-Assay of Attractants for Scholytids*. In the Canadian Entomologist. 102( ):792–796. 1970.

[7] Dale, James A., David L. Dull, and Harry S. Mosher. *$\alpha$-Methoxy-$\alpha$-trifluoromethylphenylacetic Acid, a Versatile Reagent for the Determination of Enantiomeric Composition of Alcohols and Amines*. In The Journal of Organic Chemistry, 34(9):2543–2549. September 1969.

[8] Ohta, Yoshimoto, Tsutomu Sakai and Yoshio Hirose. *Sesquiterpene Hydrocarbons from the Oil of Cubeb $\alpha$-Cubebene and $\beta$-Cubebene*. In Tetrahedron Letters. 51:6365–6370. 1966.

[9] Piers, Edward, Ronald W. Britton, and William DeWall. *Total Synthesis of ($\pm$)-$\alpha$-Cubebene and ($\pm$)-$\beta$-Cubebene*. In Canadian Journal of Chemistry. 49:12–19. 1971.

[10] Tanaka, Akiro, Reiko Tanaka, Hisashi Uda and Akira Yoshikoshi. *Synthesis of Cubebane-type Sesquiterpenoids and the Stereochemistry of Cubebol*. In Journal of the Chemical Society Perkin I. 1721–1727. 1972.

[11] Ohta, Yoshimoto, Tsutomu Sakai and Yoshio Hirose. *Sesquiterpene Hydrocarbons from the Oil of Cubeb $\beta$-Cubebene and $\beta$-Cubebene*. In Tetrahedron Letters. 51:6365–6370. 1966.

[12] Vlahov, R., M. Holub, I. Ognjanov and V. Herout. *On Terpenes. CLXXXIV. Sesquiterpenic Hydrocarbons from the Essential Oil of Mentha piperita of Bulgarian Origin*. Collection Czechoslovak Chemical Communications. 32:808—821. 1967.

Having thus described the invention, we claim:

1. A method of trapping the bark beetle *Scolytus multistriatus*, which comprises baiting a trap with an effective attractant amount of a mixture of the compounds 4-methyl-3-heptanol; 2,4-dimethyl-5-ethyl-6,8-dioxabicyclo (3.2.1) octane; and $\alpha$-cubebene, wherein the proportions of the compounds are 1:1:2–10.

2. An attractant composition for bark beetle *Scolytus multistriatus*, which comprises a mixture of the compounds 4-methyl-3-heptanol; 2,4-dimethyl-5-ethyl-6,8-dioxabicyclo (3.2.1) octane; and $\alpha$-cubebene, wherein the proportions of the compounds are 1:1:2–10.

3. A method of confusing the bark beetle *Scolytus multistriatus*, which comprises permeating the atmosphere in an area infested with said beetle with an effective attractant amount of the composition of claim 2.

4. The composition of claim 2 which further comprises an insecticidal amount of an insecticide lethal to the bark beetle *Scolytus multistriatus*, wherein the insecticide is selected from the group consisting of DDT, lindane, allethrin, chlordane, malathion, and rotenone.

* * * * *